(12) United States Patent
Bruckner et al.

(10) Patent No.: US 6,359,017 B1
(45) Date of Patent: Mar. 19, 2002

(54) DIETARY COMPOSITIONS AND METHODS

(76) Inventors: Geza Bruckner, 222 E. Eagle, Versailles, KY (US) 40383; Joseph Szabo, Ördögorom lejfö 11/B., Budapest (HU), H-1112

(*) Notice: Subject to any disclaimer, the term of this patent is extended or adjusted under 35 U.S.C. 154(b) by 0 days.

(21) Appl. No.: 09/512,577

(22) Filed: Feb. 24, 2000

Related U.S. Application Data

(60) Provisional application No. 60/121,338, filed on Feb. 24, 1999.

(51) Int. Cl.[7] .............. A61P 3/04; A61K 31/35; A61K 31/365; A61K 47/36; A61K 35/84
(52) U.S. Cl. .............. 514/909; 514/456; 514/453; 424/439
(58) Field of Search ............... 514/909, 456, 514/455; 424/439, 442

(56) References Cited

U.S. PATENT DOCUMENTS

| | | | |
|---|---|---|---|
| 4,163,746 A | 8/1979 | Feuer et al. | 260/345.2 |
| 5,654,011 A * | 8/1997 | Jackson et al. | 424/635 |

FOREIGN PATENT DOCUMENTS

| | | |
|---|---|---|
| EP | 0829261 | 3/1998 |
| EP | 0834262 | 4/1998 |
| EP | 0943245 | 9/1999 |
| JP | 9-23822 | 1/1997 |
| JP | 9-255570 | 9/1997 |
| WO | WO9965337 | 12/1999 |

OTHER PUBLICATIONS

Horn–Ross, *Cancer Causes and Control*, 6:567–573 (1995).
Mirocha et al, *Cancer Research*, 28:2319–1322 (Nov., 1968).
El–Sharkawy et al, *Xenobiotica*, 18(4):367–371 (1988).
Xu et al, *J. Nutr.* 125:2307–2315 (1995).
Lampe et al, *PSEBM*, 217:335–339 (1998).
Rowland et al, *Biochemical Society Transactions*, 27(2):304–308 (1999).
Clarkson et al, *Publication of the Society for Experimental Biology and Medicine*, 217:365–368 (1998).
Xu et al, *J. Nutr.*, 125:2307–2315 (1995).
King, *Am. J. Chem. Nutr.*, 68 (supp):1496S–1499S (1998).
Anthony et al, *J. Nutr.*, 126:43–50 (1996).
Jones et al, *Physiology & Behavior*, 50:41–45 (1991).
Flynn et al, *J. Am. Vet. Med. Assoc.*, 209(9):1572–1581 (1996).
Casanova et al, *Toxicological Sciences*, 51:236–244 (1999).
Varma et al, *Physiology & Behavior*, 68:99–107 (1999).
Fanti et al, *Osteoporos Int.*, 8:274–281 (1998).
McElroy et al, *Physiology & Behavior*, 39:361–365 (1987).
Squadrito et al, *Cardiovascular Research*, 45:454–462 (2000).
Hahn et al, *Publication of the Society for Experimental Biology and Medicine*, 126:476–479 (1967).
Ishida et al, *Biol. Pharm. Bull.*, 21(1):62–66 (1998).
Abstracts 352.4–352.8, *The FASEB Journal of Experimental Biology*, 14(4):A494 (2000).

* cited by examiner

*Primary Examiner*—Edward J. Webman
*Assistant Examiner*—Helen Nguyen
(74) *Attorney, Agent, or Firm*—Dinsmore & Shohl LLP

(57) ABSTRACT

Dietary compositions and methods employ a mammal food base and a component comprising estrogen, androgen or a mixture thereof in an amount sufficient to reduce weight gain normally incurred in the mammal type subsequent to neutering, castration, spaying, ovariectomy or ovariohysterectomy, or post menopause. Preferably, the component comprises phytoestrogen, phytoandrogen or a mixture thereof. The compositions are adapted for administration to the mammal on a regular, preferably daily, basis.

19 Claims, No Drawings

DIETARY COMPOSITIONS AND METHODS

This appln cliams benefit of Prov. No. 60/121,338 filed Feb. 24, 1999.

FIELD OF THE INVENTION

The present invention is directed to dietary compositions, particularly for mammals, including humans, dogs, cats and horses, and to methods for reducing weight gain normally incurred in mammals subsequent to neutering, castration, spaying, ovariectomy or ovariohysterectomy, or post menopause.

BACKGROUND OF THE INVENTION

Procedures including neutering, castration, spaying, ovariectomy or ovariohysterectomy are increasingly performed on dogs and cats for health related reasons and/or for population control. It is not uncommon for dogs or cats having undergone one of the aforementioned procedures to gain a significant amount of weight thereafter, and often exceed target healthy weight limits.

Weight gain incurred subsequent to ovariectomy or ovariohysterectomy procedures in other mammals, including humans, is not uncommon. Additionally, post menopausal weight gain often occurs in humans even when ovariectomy or ovariohysterectomy procedures are not performed.

While various weight reduction and weight gain prevention techniques and systems are available, such techniques and systems are typically difficult to implement on a continual basis and/or are ineffective for extended periods of time. Accordingly, a need exists for improved systems for reducing weight gain normally incurred in mammals subsequent to neutering, castration, spaying, ovariectomy or ovariohysterectomy, and/or post menopause.

SUMMARY OF THE INVENTION

It is therefore an object of the present invention to provide dietary compositions and methods which overcome disadvantages of the prior art. It is a more specific object of the invention to provide dietary compositions and methods, particularly for mammals, which reduce weight gain normally incurred in mammals subsequent to neutering, castration, spaying, ovariectomy or ovariohysterectomy, or post menopause. It is a further object of the invention to provide compositions and methods which may be easily employed by humans and with other mammals, including dogs, cats and horses.

These and additional objects and advantages are provided by the dietary compositions and methods according to the present invention. The dietary compositions according to the present invention are particularly suitable for consumption by mammals and comprise a mammal food base and a component comprising estrogen, androgen or a mixture thereof in an amount sufficient to reduce weight gain normally incurred in the mammal type subsequent to neutering, castration, spaying, ovariectomy or ovariohysterectomy, or in a post menopausal phase, when the dietary composition is administered on a daily or otherwise regular basis. In preferred embodiments, the component comprises phytoestrogen, phytoandrogen or a mixture thereof. The methods according to the present invention are directed to reducing weight gain normally occurring in a mammal subsequent to neutering, castration, spaying, ovariectomy or ovariohysterectomy, or post menopause. These methods comprise administering to the mammal on a daily or otherwise regular basis a dietary composition comprising a mammal food base and a component comprising estrogen, androgen or a mixture thereof in an amount sufficient to reduce weight gain normally incurred in the mammal type subsequent to neutering, castration, spaying, ovariectomy or ovariohysterectomy, or post menopause, when the dietary composition is administered on a daily or otherwise regular basis. In preferred embodiments of the methods, the component comprises phytoestrogen, phytoandrogen or a mixture thereof.

Further objects and advantages provided by the compositions and methods according to the present invention will be more fully apparent in view of the following detailed description.

DETAILED DESCRIPTION

The dietary compositions according to the present invention are suitable for consumption by mammals and are intended to reduce weight gain normally incurred in the mammal type subsequent to neutering, castration, spaying, ovariectomy or ovariohysterectomy, or post menopause, particularly when the dietary composition is administered on a daily or otherwise regular basis. The compositions comprise a food base and a component comprising estrogen, androgen, or a mixture thereof. The estrogen and androgen which are suitable for use in the compositions and methods of the present invention may be obtained or derived from any natural or synthetic source which exhibits estrogenic or androgenic activity, respectively.

In prefered embodiments, phytoestrogen, phytoandrogen or a mixture thereof is employed. The phytoestrogen and phytoandrogen preferred for use in the present compositions may be derived from various plants. Preferred plant sources of phytoestrogen comprise soybean, or its isolated products, eg., soy protein isolate or soy hypocotyls, and flax seed, or its isolated products, eg., flax protein isolate, although other plants such as red clover and other clovers, alfalfa, barrel medic, chickpeas, lentils, beans, Hibiscus rosa sinensis and/or grapes may be employed. In addition to the aforementioned phytoestrogen sources, phytoandrogens may be found in sources such as *Serenoa repens, Dalbergia cochinchinensis, Brosimum rubescens, Striga orobanchioides*, and *Azadurachta indica*. These examples are illustrative only and do not constitute a complete list. One skilled in the art will recognize that other phytoestrogen and/or phytoandrogen sources may be employed in the dietary compositions and methods of the present invention. In further preferred embodiments, the phytoestrogen and/or phytoandrogen are derived from soy beans, or flax seeds. Examples of specific groups of phytoestrogen compounds suitable for use in the compositions of the present invention include, but are not limited to, isoflavones, lignans, coumestans, resorcylic acid lactones, and mixtures thereof. Daidzein, genistein and coumesterol are particularly preferred sources of phytoestrogen for use in the dietary compositions of the present invention. Other preferred sources are formononetin, genistin, daidzin, ononin, sissotrin, resveratrol and biochanin A. One skilled in the art will appreciate that glycosides such as daidzin and genistin convert to the aglycone compounds, daidzein and genistein, upon fermentation.

In alternate embodiments, the estrogen or androgen may be derived from fungal, microbial and other naturally occurring sources exhibiting estrogenic or adrogenic activity, respectively, or these components may be synthetically derived in accordance with methods known in the art. In this regard, the conversion of an isoflavone glycoside to the aglycone form by fermentation is a preferred example of synthetically derived components.

The food base with which the estrogen and/or androgen are combined may comprise any suitable food component including, but not limited to, a food of animal origin, for example, meat or a milk product, or of plant origin, including a cereal, for example oat or bran, a starch, mono, di, poly or oligosaccharides, an oil meal, or other cellulosic material, or mixtures thereof. Selection of a specific food base for use in the compositions of the present invention will depend, in part, on the type of dietary composition which is desired. For example, for dietary compositions suitable for administering to humans, the food base may conveniently comprise a milk product, a cereal product or the like to be administered alone or as an additive in connection with other types of foods, for example as a sauce, dressing, powder or the like. As a dietary composition for administering to pets such as dogs and/or cats, the dietary composition may be provided in the form of a biscuit or other treat, or in the form of a complete and balanced food.

In this regard, the form of dietary composition, i.e., main component or additive, which is selected will also influence the amount of the estrogen and/or androgen which is employed therein. In a preferred embodiment, the dietary composition comprises from about 0.001 to about 10 weight percent, based on the weight of the composition, of estrogen and/or androgen, and preferably comprises from about 0.001 to about 10 weight percent of phytoestrogen and/or phytoandrogen. More preferably, the dietary composition comprises from about 0.01 to about 10 weight percent, based on the weight of the composition, of estrogen and/or androgen, preferably phytoestrogen and/or phytoandrogen.

In the methods for reducing weight gain normally incurred in a mammal subsequent to neutering, castration, spaying, ovariectomy or ovariohysterectomy, or post menopause, according to the present invention, a dietary composition is administered to the mammal on a routine or regular basis, preferably on a daily basis. The dietary composition comprises a mammal food base and a component comprising estrogen, androgen or a mixture thereof in an amount sufficient to reduce weight gain normally incurred in the mammal type subsequent to neutering, castration, spaying, ovariectomy or ovariohysterectomy, or post menopause, when the dietary composition is administered to the mammal on a daily or otherwise regular basis. In preferred embodiments of the methods, the component comprises phytoestrogen, phytoandrogen or a mixture thereof. In a further preferred embodiment, the dietary composition is administered to the mammal in an amount sufficient to provide estrogen, androgen or a mixture thereof to the mammal in an amount of from about 0.001 to 100 mg per gram of the total diet administered to the mammal. More preferably, the dietary composition is administered to the mammal in an amount sufficient to provide estrogen, androgen or a mixture thereof to the mammal in an amount of from about 1 to about 25,000 $\mu$g per gram of total diet administered to the mammal, and even more preferably in an amount of from about 60 to about 4,000 $\mu$g per gram of total diet administered to the mammal.

These amounts of estrogen and/or androgen may conveniently be supplied by administering soy bean-derived or soy protein-containing products, i.e., soy protein isolate or soy hypocotyl, and/or flax seed products or flax protein products, i.e., flax protein isolate, to the mammal in an amount, for example, of from about 1% to about 50% of the total diet of the mammal, and preferably in an amount of from about 1% to about 35% by weight of the diet when the method is directed to reducing weight gain in a human. Suitable soybean or soy protein isolate product amounts, or fermentation product amounts, wherein an isoflavone glycoside has been converted to an aglycone, would be in the range of from about 1 to about 1,000 grams soy protein per day, with amounts of 5 to 500 grams soybean derived products or soy protein isolate and/or flax seed derived products or flax protein isolate per day being preferred for methods for reducing weight gain in humans. Alternatively, in embodiments wherein the estrogen and/or androgen are derived from fungal, microbial or other natural or synthetic sources, the sources may suitably comprise from about 0.005% to about 15% by weight of the total diet administered to the mammal, with 0.005% to about 10% by weight being preferred when the methods are directed to reducing weight gain in humans. Suitable amounts of estrogen and/or androgen derived from fungal, microbial or other natural sources, are preferably administered to the mammal in an amount sufficient to provide from about 0.1 to about 100 mg of estrogen and/or androgen per kilogram of the mammal's body weight.

The dietary compositions may be administered in an amount sufficient to provide estrogen, androgen or a mixture thereof to the mammal in an amount of from about 0.001 to about 100 mg per kilogram of the mammal's body weight, with the amount more preferably being in the range of from about 0.005 to about 50 mg per kilogram of the mammal's body weight when the methods are directed to reducing weight gains in humans, dogs, cats or horses. These amounts are preferably administered on a regular or routine basis, more preferably on a daily basis. To further illustrate more specific embodiments of the invention, when the estrogen comprises daidzein, genistein or a phytoestrogen of a similar structure, the dietary composition is preferably administered to the mammal in an amount sufficient to provide from about 0.1 to about 80 mg daidzein and/or genistein per kilogram of the mammal's body weight, with a range of from about 0.1 to about 60 mg per kilogram being preferred for methods directed to reducing weight gains in humans. Further, when the estrogen comprises coumesterol or a phytoestrogen of a similar structure, the dietary composition is administered to the mammal in an amount sufficient to provide the phytoestrogen in an amount of from about 0.5 to about 50 mg per kilogram of the mammal's body weight, with the range of from about 0.1 to about 30 mg per kilogram of body weight being preferred when the method is directed to reducing weight gains in humans.

In further embodiments, the dietary compositions of the present invention further include vitamins, minerals, or salts thereof, colorants, preservatives and/or other additional components which are conventionally administered to mammals. Examples of suitable minerals include calcium, phosphorous, potassium, sodium, iron, copper, zinc, manganese, iodine, selenium and the like, while suitable vitamins include vitamin A, various B vitamins, vitamin C, vitamin D and/or vitamin E. Additional conventional dietary supplements may also be included, for example, inulin, folic acid, biotin and the like.

In specific embodiments, the dietary compositions include one or more calcium salts, one or more peptides and/or amino acids, and/or a tocopherol compound. Suitably, calcium salts are included in the dietary composition in an amount sufficient to provide the mammal from about 100 to about 3,000 mg calcium salt per day, or from about 10 to about 100 mg per kilogram of the mammal's body weight. A preferred peptide comprises L-carnitine. Amino acids and/or di and tripeptides are preferably included in the dietary composition in an amount of from about 0.1 to about 400 ppm or in an amount sufficient to provide from about 0.05 to about 15 mg amino acid per kilogram of the mammal's body weight, per day. A tocopherol compound such as alpha tocopherol or a natural tocopherol mixture may suitably be employed in an amount sufficient to administer from about 1 to about 500 mg to the mammal per day, or from about 1 to about 10 mg per kilogram of the mammal's body weight, per day.

The compositions and methods according to the present invention are further exemplified by the following Examples. In the Examples and throughout the present specification, parts and percentages are by weight unless otherwise specified.

EXAMPLE 1

Dietary compositions according to the present invention are prepared comprising from about 0.001 to about 200 parts by weight one or more phytoestrogen compounds, from about 0.5 to about 100 parts by weight of L-carnitine, from about 0.1 to about 500 parts by weight of calcium salt, from about 0.5 to 60 parts by weight of alpha tocopherol or mixed tocopherols, and from about 0.1 to about 100 parts by weight of a vehicle comprising oligosaccharides, starch, protein, fat and/or other fibers or cellulose components. Additional compositions are prepared wherein from about 1 to about 100 parts by weight phytoestrogen compounds and from about 1 to about 100 parts by weight of androgen compounds are employed in combination with the indicated amounts of L-carnitine, calcium salt, tocopherol and vehicle. These compositions are suitable for use in the methods of the present invention for reducing weight gain normally incurred in a mammal subsequent to neutering, castration, spaying, ovariectomy or ovariohysterectomy, or post menopause, on a daily or otherwise regular basis by administering from about 0.01 to about 4,000 grams or from about 0.01 to about 50 percent by weight of the total diet administered to the mammal.

EXAMPLE 2

Dietary compositions in the form of food supplements for dogs and cats are prepared including the ingredients in the amounts set forth in Table 1. In accordance with the present methods, the dog supplement is administered in an amount of about 10% of the total diet of the dog, and, for a 35 kilogram dog, in an amount of about 40 g per day. The cat supplement is similarly administered to the diet in an amount of about 10% of the total diet of the cat and in an amount of about 5 to about 10 g per day. The supplements are administered in order to reduce weight gains typically incurred in dogs and cats following neutering, castration, spaying, ovariectomy or ovariohysterectomy.

TABLE 1

| Ingredients provided per day | Dog Supplement | Cat Supplement |
|---|---|---|
| Daidzein, genistein or other phytoestrogen (mg) | 100–4000 (1500) | 20–400 (200) |
| Inulin (mg) | 5000 | 500 |
| Ca (mg) | 2870 | 570 |
| P (mg) | 2150 | 430 |
| K (mg) | 2150 | 290 |
| Na (mg) | 800 | 200 |
| Fe (mg) | 16 | 6 |
| Cu (mg) | — | 4 |

TABLE 1-continued

| Ingredients provided per day | Dog Supplement | Cat Supplement |
|---|---|---|
| Zn (mg) | 2 | 0.4 |
| Mn (mg) | 3 | 0.4 |
| I (mg) | 0.3 | 0.03 |
| Se (mg) | 0.1 | 0.01 |
| Vitamin A (IU) | 1000 | 240 |
| Vitamin D (IU) | 400 | 50 |
| Vitamin E (IU) | 50 | 10 |
| Thiamine (mg) | 5 | 1 |
| Riboflavin (mg) | 2 | 1 |
| Pantothenic acid (mg) | 15 | 5 |
| Niacin (mg) | 15 | 5 |
| Pyridoxine (mg) | 2 | 1 |
| Folic acid (mg) | 0.1 | 0.05 |
| Biotin (mg) | 0.2 | 0.1 |
| Choline (mg) | 400 | 50 |
| Vitamin C (mg) | 5 | 2 |
| Vehicle (mg) | 20,000 | 10,000 |

EXAMPLE 3

Dietary compositions in the form of dog and cat treats are prepared using the components and amounts specified in Table 2. The dog supplement is administered to a 35 kilogram dog in an amount of about 4 g per day while the cat supplement is administered to a 4 kilogram cat in an amount of about 2 g per day, in accordance with the methods of the present invention.

TABLE 2

| Ingredients | Dog Supplement | Cat Supplement |
|---|---|---|
| Fish meal (herring) mg | 20,000 | 10,000 |
| Genistein, daidzein or other phytoestrogen (mg) | 100–2000 (750) | 20–300 (150) |
| Flax meal (mg) | 1000 | 500 |
| Inulin (mg) | 1000 | 100 |
| Carnitine (mg) | 50 | 15 |
| Ca (mg) | 400 | 150 |
| P (mg) | 350 | 120 |
| Fe (mg) | 5 | 2 |
| Cu (mg) | .2 | .02 |
| Zn (mg) | 2 | 0.4 |
| Mn (mg) | 3 | 0.4 |
| Se (mg) | 0.01 | 0.001 |
| Vitamin A (IU) | 400 | 120 |
| Vitamin D (IU) | 40 | 5 |
| Vitamin E (IU) | 10 | 2 |
| Thiamine (mg) | 1 | .1 |
| Riboflavin (mg) | .2 | .1 |
| Pantothenic acid (mg) | 1.5 | .5 |
| Niacin (mg) | 1.5 | .5 |
| Pyridoxine (mg) | .2 | .1 |
| Folic acid (mg) | .01 | .005 |
| Biotin (mg) | .02 | .01 |
| Choline (mg) | 40.0 | 5.0 |
| Vitamin C (mg) | .5 | .2 |
| Arginine (mg) | 5 | 2 |
| Methionine (mg) | 50 | 25 |

EXAMPLE 4

Dietary compositions in the form of a liquid drink and a dry powder, respectively, are prepared using the components in the amounts specified in Table 3. These compositions are administered to humans in order to reduce weight gains typically incurred following ovariectomy or ovariohysterectomy or post menopause and are administered in an amount of from about 1 to about 1,000 ml per day or from about 0.1 to about 100 grams per kilogram body weight, per day.

TABLE 3

| Ingredients | Liquid Formulation | Dry Formulation |
| --- | --- | --- |
| Skim milk | 88% | — |
| Skim milk powder | — | 64% |
| Flax and/or Soy meal (47% protein) | 9.0% | 29.5% |
| Fructose oligosaccharide | 1.0% | 2.0% |
| Conjugated linoleic acid | 0.6% | 1.70% |
| Soybean oil | .45% | 1.75% |
| Vitamin premix | 1.0% | 1.0% |
| Genistein, Daidzein, and/or Coumesterol or other estrogenic compound | 0.05% | 0.05% |

The foregoing examples and various preferred embodiments of the present invention set forth herein are provided for illustrative purposes only and are not intended to limit the scope of the invention defined by the claims. Additional embodiments of the present invention and advantages thereof will be apparent to one of ordinary skill in the art and are within the scope of the invention defined by the following claims.

We claim:

1. A method for reducing weight gain normally incurred in a mammal subsequent to neutering, castration, spaying, ovariectomy or ovariohysterectomy, or post menopause, comprising administering to the mammal on a regular basis a dietary composition comprising a mammal food base and a component comprising a phytoestrogen, phytoandrogen or a mixture thereof in an amount sufficient to reduce weight gain normally incurred in the mammal type subsequent to neutering, castration, spaying, ovariectomy or ovariohysterectomy, or post menopause, when the dietary composition is administered to the mammal on a regular basis.

2. A method according to claim 1, wherein the phytoestrogen comprises isoflavone, lignan, coumestan, resorcylic acid lactone, or mixtures thereof.

3. A method according to claim 1, wherein the phytoestrogen or phytoandrogen is derived from soy bean or flax seed, or protein products thereof.

4. A method according to claim 1, wherein the mammal food base comprises a food of animal origin, a cereal, a starch, or mixtures thereof.

5. A method according to claim 1, wherein the dietary composition is administered in an amount sufficient to provide estrogen, androgen or a mixture thereof to the mammal in an amount of from about 0.001 mg to about 100 mg per gram of total diet administered to the mammal.

6. A method according to claim 1, wherein the dietary composition is administered in an amount sufficient to provide phytoestrogen, phytoandrogen or a mixture thereof to the mammal in an amount of from about 0.001 mg to about 100 mg per gram of total diet administered to the mammal.

7. A method according to claim 1, wherein the dietary composition is administered in an amount sufficient to provide phytoestrogen, phytoandrogen or a mixture thereof to the mammal in an amount of from about 1 $\mu$g to about 25,000 $\mu$g per gram of total diet administered to the mammal.

8. A method according to claim 1, wherein the dietary composition is administered in an amount sufficient to provide phytoestrogen, phytoandrogen or a mixture thereof to the mammal in an amount of from about 60 $\mu$g to about 4000 $\mu$g per gram of total diet administered to the mammal.

9. A method according to claim 1, wherein the dietary composition is administered in an amount sufficient to provide phytoestrogen, phytoandrogen or a mixture thereof to the mammal in an amount of from about 0.001 mg to about 100 mg per kilogram of the mammal's bodyweight.

10. A method according to claim 1, wherein the dietary composition is administered in an amount sufficient to provide phytoestrogen, phytoandrogen or a mixture thereof to the mammal in an amount of from about 0.005 mg to about 50 mg per kilogram of the mammal's bodyweight.

11. A method according to claim 1, wherein the mammal is a human.

12. A method according to claim 1, wherein the mammal is a dog or cat.

13. A method according to claim 1, wherein the mammal is a horse.

14. A method according to claim 1, wherein the phytoestrogen comprises daidzin, genistin or coumesterol.

15. A method according to claim 1, wherein the phytoestrogen comprises daidzein, genistein, or a mixture thereof.

16. A method according to claim 1, wherein the dietary composition is administered to the mammal on a daily basis.

17. A method for reducing weight gain normally incurred in a mammal subsequent to neutering, castration, spaying, ovariectomy or ovariohysterectomy, or post menopause, comprising administering to the mammal on a regular basis a dietary composition comprising a mammal food base and a component comprising an estrogen or androgen derived from a fungal or microbial source, or a mixture of estrogen or androgen derived from a fungal or microbial source, in an amount sufficient to reduce weight gain normally incurred in the mammal type subsequent to neutering, castration, spaying, ovariectomy or ovariohysterectomy, or post menopause, when the dietary composition is administered to the mammal on a regular basis.

18. A method according to claim 17, wherein the dietary composition is administered in an amount sufficient to provide estrogen, androgen or a mixture thereof to the mammal in an amount of from about 1 $\mu$g to about 25,000 $\mu$g per gram of total diet administered to the mammal.

19. A method according to claim 17, wherein the dietary composition is administered in an amount sufficient to provide estrogen, androgen or a mixture thereof to the mammal in an amount of from about 60 $\mu$g to about 4000 $\mu$g per gram of total diet administered to the mammal.

* * * * *

UNITED STATES PATENT AND TRADEMARK OFFICE
CERTIFICATE OF CORRECTION

PATENT NO. : 6,359,017 B1  Page 1 of 1
DATED : March 19, 2002
INVENTOR(S) : Geza Bruckner et al.

It is certified that error appears in the above-identified patent and that said Letters Patent is hereby corrected as shown below:

Column 7,
Line 46, change "claim 1" to -- claim 17 --.

Signed and Sealed this

Eighth Day of October, 2002

Attest:

Attesting Officer

JAMES E. ROGAN
Director of the United States Patent and Trademark Office